(12) United States Patent
Sundaresan et al.

(10) Patent No.: US 7,075,424 B1
(45) Date of Patent: *Jul. 11, 2006

(54) SYSTEM FOR DAMAGE LOCATION USING A SINGLE CHANNEL CONTINUOUS ACOUSTIC EMISSION SENSOR

(75) Inventors: Mannur J. Sundaresan, Greensboro, NC (US); Anindya Ghoshal, Middletown, CT (US); Mark J. Schulz, West Chester, OH (US)

(73) Assignee: North Carolina A&T State University, Greensboro, NC (US)

( * ) Notice: Subject to any disclaimer, the term of this patent is extended or adjusted under 35 U.S.C. 154(b) by 40 days.

This patent is subject to a terminal disclaimer.

(21) Appl. No.: 10/887,460

(22) Filed: Jul. 8, 2004

(51) Int. Cl.
*G08B 23/00* (2006.01)

(52) U.S. Cl. ............... 340/500; 340/506; 340/517; 340/679; 340/683

(58) Field of Classification Search ............ 340/506, 340/500, 517, 522, 679, 683, 690
See application file for complete search history.

(56) References Cited

U.S. PATENT DOCUMENTS

| | | | | |
|---|---|---|---|---|
| 3,787,700 | A * | 1/1974 | Chasson | 250/559.25 |
| 5,894,651 | A | 4/1999 | Dvorsky et al. | 310/344 |
| 5,929,315 | A | 7/1999 | Dunegan | 73/1.82 |
| 5,932,807 | A * | 8/1999 | Mallart | 73/641 |
| 6,006,163 | A | 12/1999 | Lichtenwalner et al. | 702/36 |
| 6,076,405 | A * | 6/2000 | Schoess | 73/587 |
| 6,370,964 | B1 * | 4/2002 | Chang et al. | 73/862.046 |
| 6,399,939 | B1 * | 6/2002 | Sundaresan et al. | 250/231.1 |
| 6,923,062 | B1 * | 8/2005 | Franz et al. | 73/514.38 |

OTHER PUBLICATIONS

Sundaresan and Shankar, The Use of AET for Classifying Failure Modes in Composite Materials, ASME Winter Annual Meeting, New Orleans, LA, Nov. 23-Dec. 3, 1993.

Sun, et al., Structural Frequency Response Function Acquisition Via Electric Impedance Measurement of Surface-Bonded Piezoelectric Sensor/Actuator from the American Insitute of Aeronautics and Astronautics, pp. 3450-3458, 1995.

Prosser, et al., Advanced Waveform Based Acoustic Emission Detection of Matrix Cracking in Composites; Materials Evaluation, vol. 53(9), pp. 1052-1058, Sep. 1995.

(Continued)

*Primary Examiner*—Daryl C Pope
(74) *Attorney, Agent, or Firm*—MacCord Mason PLLC

(57) ABSTRACT

A sensor array for non-destructively monitoring a structure to detect a critical structural event. The sensor array includes a plurality of discrete sensor nodes, each of the discrete sensor nodes producing an electrical signal in response to a structural event. A signal adder is electrically connected to the plurality of discrete sensor nodes for receiving and combining the electrical signal from each of the discrete sensor nodes to form a single sensor array output signal. A signal processing module then receives and processes the single sensor output signal. In the preferred embodiment, the signal processing module uses the time interval between the electrical signals from each of the discrete sensor nodes formed into a single sensor array output signal to calculate the location of the critical structural event. Also, in the preferred embodiment, a data collection system is located downstream of the sensor processing module.

45 Claims, 12 Drawing Sheets

OTHER PUBLICATIONS

ACX (Active Control eXperts); Information from the Internet; copyright 1996-2000.

Schoess, et al, Rotor Acoustic Monitoring System (RAMS)-A Fatigue Crack Detection System American Helicopter Society (AHS) FORUM 53, Virginia Beach, VA, May 1, 1997.

Hagood and Pizzochero, Residual Stiffness and Actuation Properties of Peizoelectric Composites: Theory and Experiment from Journal of Intelligent Material Systems and Structures, vol. 8, Sep. 1997.

Chee et al., Review on the Modelling of Piezoelectric Sensors and Actuators Incorporated in Intelligent Structures from the Journal of Intelligent Material Systems and Structures, vol. 9—Jan. 1998.

Bent and Hagood, Piezoelectric Fiber Composites with Interdigitated Electrodes; Journal of Intelligent Material Systems and Structures, vol. 8, Oct. 1998.

Prosser, Acoustic Emission Structural Health Monitoring, Aviation Safety NRA Meeting, Dec. 17, 1998.

NASA, Tech Briefs, vol. 23, No. 10, Oct. 1999.

Continuum Control Corp., An innovative provider of piezoelectric components and integrated systems for motion control, and vibration suppression, 1999.

Sundaresan et al., Damage Detection Using A Layer Vibrometer and Active Fiber Composite Patch, Sixth Annual International Conference on Composites Engineering, Orlando, FL, Jun. 27-Jul. 3, 1999.

Schulz, et al., Distributed Sensing for Health Monitoring of Composite Materials, Composites in the Transportation Industry Conference, Feb. 14-18, 2000.

Sundaresan, M.J., et al., "Linear Location of Acoustic Emission Sources with a Single Channel Distributed Sensor," Journal of Intelligent Material Systems and Structures, vol. 12, No. 10, pp. 689-700, Oct. 2001. (Copy unavailable).

Cordell, Tobey M., Life management of aging air force aircraft: NDE prespective, SPIE vol. 2455, pp. 34-44, 1995.

Komsky and Achenbach, Ultrasonic imaging for corrosion and fatigue cracks in multilayered airplace structures; article from Center for Quality Engineering and Failure Prevention, SPIE vol. 2945, pp. 380-388, 1996.

Acoustic Emission Sensing Using Piezoceramic and Active Fiber Composite Patches; article from University of Missouri; undated *** Copy not available.

Blanas et al., Article entitled Active Composite Materials and Damage Monitoring; undated.

CeraNova Corporation; Active Composites for Smart Structures; information from internet; copyright 2000.

Lichtenwainer, et al., Active Damage Interrogation System for Structural Health Monitoring; SPIE vol. 3044, pp. 186-194, 1997.

Seydel and Chang, Implementation of a Real-Time Impact Identification Technique for Stiffened Composite Panels; Dept. of Aeronautics and Astronautics, Stanford University.

Wang and Chang, Built-In Diagnostics for Impact Damage Identification of Composite Structures; Stanford University; undated.

Ghoshal, A.; Sundaresan, M. J.; Schulz, M. J.; Pai, P. F. "Structural Health Monitoring Techniques for Wind Turbine Blades," Journal of Industrial Aerodynamics and Wind Power Engineering, vol. 85, pp. 309-324, 2000.

* cited by examiner

SYSTEM FOR DAMAGE LOCATION USING A SINGLE CHANNEL CONTINUOUS ACOUSTIC EMISSION SENSOR

BACKGROUND OF THE INVENTION (1) Field of the Invention

The present invention relates generally to non-destructive testing and, more particularly, to a sensor array for non-destructively monitoring a structure to detect a critical structural event and calculate the location of the critical structural event.

(2) Description of the Prior Art

The performance of modern-day military helicopters, missiles, tanks, aircraft, and other static or dynamic structures is critically dependent on the reliability of advanced composite materials and heterogeneous armor materials. There has been a reluctance to deploy such high performance materials in critical structural applications because of their susceptibility to in-service damage. The damage occurring in these materials may be difficult to track and can propagate quickly during operation of the vehicle or structure, resulting in the loss of the entire vehicle.

Conventional non-destructive evaluation techniques are labor intensive, expensive, error prone, and unworkable for efficient integration into composite and heterogeneous structures. Autonomous integrated Structural Health Monitoring (SHM) techniques are a revolutionary concept in the maintenance of structures. SHM techniques continuously monitor the condition of a structure. Various approaches for SHM under development use piezoceramic sensors and actuators that require separate wiring connections for each sensor and actuator element, storage of pre-damage data for each sensor, and instrumentation for active generation and sensing of diagnostic signals. When the structural geometry is complex—e.g., either the structure has varying thickness, curvature, ribs, joints, or heterogeneous materials, or damage is located near boundaries of the structure—it becomes difficult to detect small damage using SHM methods. In addition, the number of sensor circuits and computations required increases the overall complexity and cost of the structure.

One approach to this problem is to integrate many fiber-optic strain gauges directly within the structural material. An optical fiber with twenty or more Bragg gratings can measure static and dynamic strains at discrete locations on the structure. An optical analyzer can multiplex over each fiber and each grating to measure strains at a large number of points on a structure. This approach is being implemented on bridges, pressure tanks and other structures. However, fiber optic sensors have limitations when applied to monitoring complex composite structures where damage can occur anywhere on the structure and in any direction. For example, discrete strain measurements can miss damage because the measurement is very localized at the fiber/grating. In addition, an optical analyzer using multiplexing and multiple connections is expensive; measurements are not simultaneous and the frequency bandwidth may be too low to sense Acoustic Emission (AE) signals.

AE sensors are presently suitable for detection of damage at "hot spots." The use of AE measurements for SHM of large structures may have certain advantages since it is a passive sensing technique. Passive sensing methods are simpler and may be more practical than using active interrogation methods. However, present passive acoustic emission and monitoring techniques require bulky instrumentation with numerous channels, long connections, and centralized data analysis. It may be impractical to embed these systems on the structure to operate in the field. Another limitation is that AE waveforms from such sensors are too complicated for purposes of source characterization.

U.S. Pat. No. 6,399,939 issued Jun. 4, 2002 to Sudaresan et al. discloses a sensor array apparatus and method for reducing the number of sensors and instrumentation channels required, by an order of magnitude, while retaining the sensitivity in the high frequency range to detect incipient damage in the structure. The disclosure of this patent and its cited references is hereby incorporated by reference in its entirety.

Thus, there remains a need for a new and improved system for non-destructively monitoring a structure to detect a critical structural event using a single channel continuous acoustic emission sensor that provide sufficient spatial coverage to efficiently sense AE signals while, at the same time, may be used to calculate the location of the critical structural event.

SUMMARY OF THE INVENTION

The present invention is directed to a sensor array for non-destructively monitoring a structure to detect a critical structural event. The sensor array includes a plurality of discrete sensor nodes, each of the discrete sensor nodes producing an electrical signal in response to a structural event. A signal adder is electrically connected to the plurality of discrete sensor nodes for receiving and combining the electrical signal from each of the discrete sensor nodes to form a single sensor array output signal. A signal processing module then receives and processes the single sensor output signal. In the preferred embodiment, the signal processing module uses the time interval between the electrical signals from each of the discrete sensor nodes formed into a single sensor array output signal to calculate the location of the critical structural event. Also, in the preferred embodiment, a data collection system is located downstream of the sensor processing module.

In the preferred embodiment, the plurality of discrete sensor nodes may be further divided into discrete subgroups, each of the discrete subgroups located at a different structural location. The plurality of discrete sensor nodes may also be electrically connected in series thereby forming a continuous series connection between each of the discrete sensor nodes.

In one embodiment, each of the discrete sensor nodes includes a chemical sensor. In another embodiment, each of the discrete sensor nodes includes an accelerometer. Preferably, each of the discrete sensor nodes includes a piezoceramic sensor. The piezoceramic sensor may further include a plurality of piezoceramic fibers arranged in a planer array wherein the piezoceramic fibers are aligned substantially parallel to each other.

The signal adder and the signal processing module preferably are connected in series. In addition, the sensor array may further include a signal amplifier connected between the signal adder and the signal processing module. In the preferred embodiment, the signal amplifier is an impedance matched amplifier. Also, the sensor array may further include a plurality of individual node signal amplifiers connected between each of the discrete sensor nodes and the signal processing module. In the preferred embodiment, each of the node signal amplifiers is an impedance matched amplifier.

The sensor array may further include a guard array which, in the preferred embodiment, the guard array is a guard ring.

Also, in the preferred embodiment, the signal processing module includes an input, a filter and an output on a timed scale to calculate the location of the critical structural event. The filter may be at a predetermined band width and, in the preferred embodiment, the predetermined band width is calculated according to the Lamb wave propagation characteristics resulting from the acoustic emission pulse at the source location and by identifying one or more non dispersive modes of this lamb wave to locate this acoustic emission source. Alternatively, it may be calculated using an electronic tag attached to each sensor that provides the ID number of the first hit sensor. The data collection system may include a database module. In addition, the data collection system may further include an exception reporting module. In the preferred embodiment, the exception reporting module includes means for setting a predetermined threshold value and means for sending an alarm when the predetermined threshold value is met. Also, the exception reporting module may further include means for identifying the location of the alarm.

Accordingly, one aspect of the present invention is to provide a sensor array for non-destructively monitoring a structure to detect a critical structural event, the sensor array including: a plurality of discrete sensor nodes, each of the discrete sensor nodes producing an electrical signal in response to a structural event; a signal adder electrically connected to the plurality of discrete sensor nodes, the signal adder receiving and combining the electrical signal from each of the discrete sensor nodes to form a single sensor array output signal; and a signal processing module for receiving and processing the single sensor output signal.

Another aspect of the present invention is to provide a sensor array for non-destructively monitoring a structure and to detect a critical structural event, the sensor array including: a signal adder electrically connected to a plurality of discrete sensor nodes, the signal adder receiving and combining the electrical signal from each of the discrete sensor nodes to form a single sensor array output signal; and a signal processing module for receiving and processing the single sensor output signal, whereby the signal processing module uses the time interval between the electrical signals from each of the discrete sensor nodes formed into a single sensor array output signal to calculate the location of the critical structural event.

Still another aspect of the present invention is to provide a sensor array for non-destructively monitoring a structure to detect a critical structural event, the sensor array including: a plurality of discrete sensor nodes, each of the discrete sensor nodes producing an electrical signal in response to a structural event; a signal adder electrically connected to the plurality of discrete sensor nodes, the signal adder receiving and combining the electrical signal from each of the discrete sensor nodes to form a single sensor array output signal; a signal processing module for receiving and processing the single sensor output signal, whereby the signal processing module uses the time interval between the electrical signals from each of the discrete sensor nodes formed into a single sensor array output signal to calculate the location of the critical structural event; and a data collection system downstream of the sensor processing module.

These and other aspects of the present invention will become apparent to those skilled in the art after a reading of the following description of the preferred embodiment when considered with the drawings.

DESCRIPTION OF THE PREFERRED EMBODIMENTS

Figure 1:
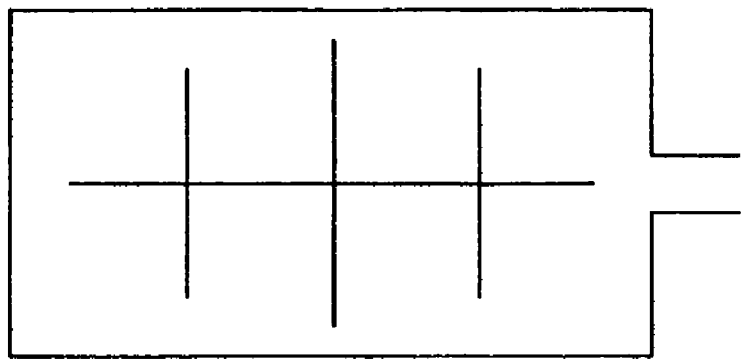
FIG. 1 is a top elevation view of a prior art, bi-directional/single node PZT wafer sensor.
Figure 2:
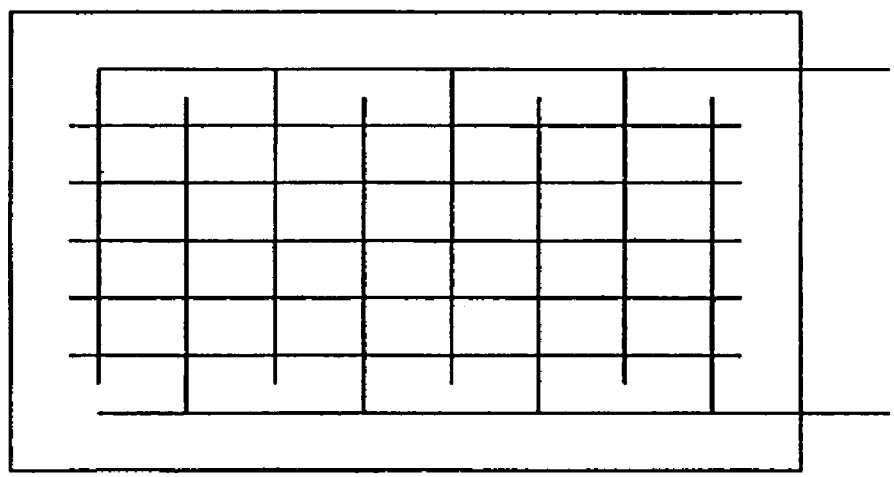
FIG. 2 is a top elevation view of a prior art, uni-directional/single node PZT fiber sensor.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Figure 3:
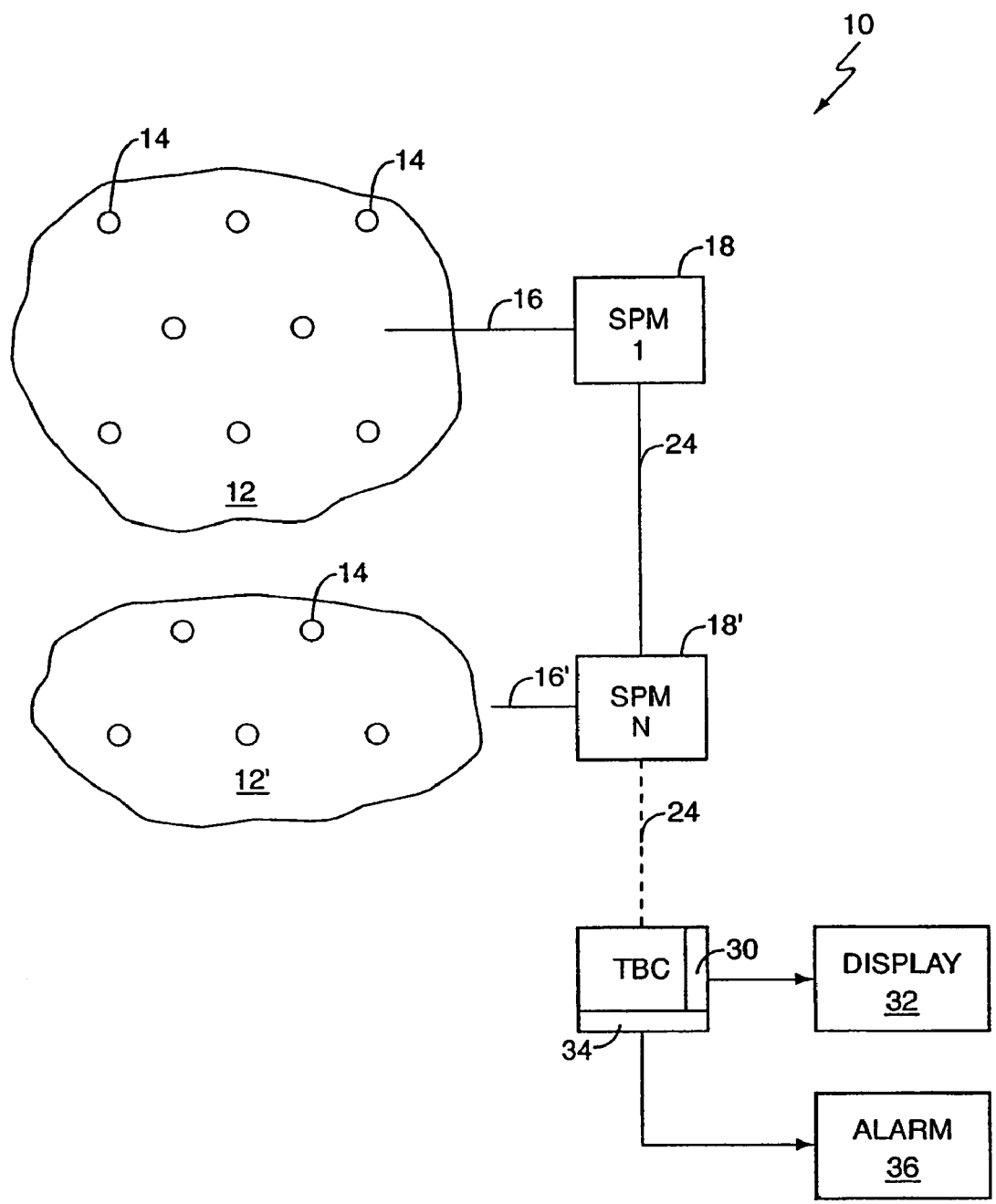
FIG. 3 is a block diagram of a sensor array including a plurality of discrete sensor nodes combined into a single output constructed according to the earlier invention disclosed in commonly owned U.S. Pat. No. 6,399,939.

Referring now to the drawings in general and FIG. 3 in particular, it will be understood that the illustrations are for the purpose of describing a preferred embodiment of the invention and are not intended to limit the invention thereto. As best seen in FIG. 3, a sensor array, generally designated 10, is shown constructed according to the earlier invention disclosed in commonly owned U.S. Pat. No. 6,399,939. The sensor array 10 includes three major sub-assemblies: a unit cell 12 having a plurality of discrete sensor nodes 14; a signal adder for combining the output of each of the discrete sensor nodes 14 into a single output 16; and at least one signal processing module 18. Similar signal processing units are commercially available. Among the manufacturers of such units is Endevco Corporation, located in San Juan Capistrano, Calif.

Figure 4:
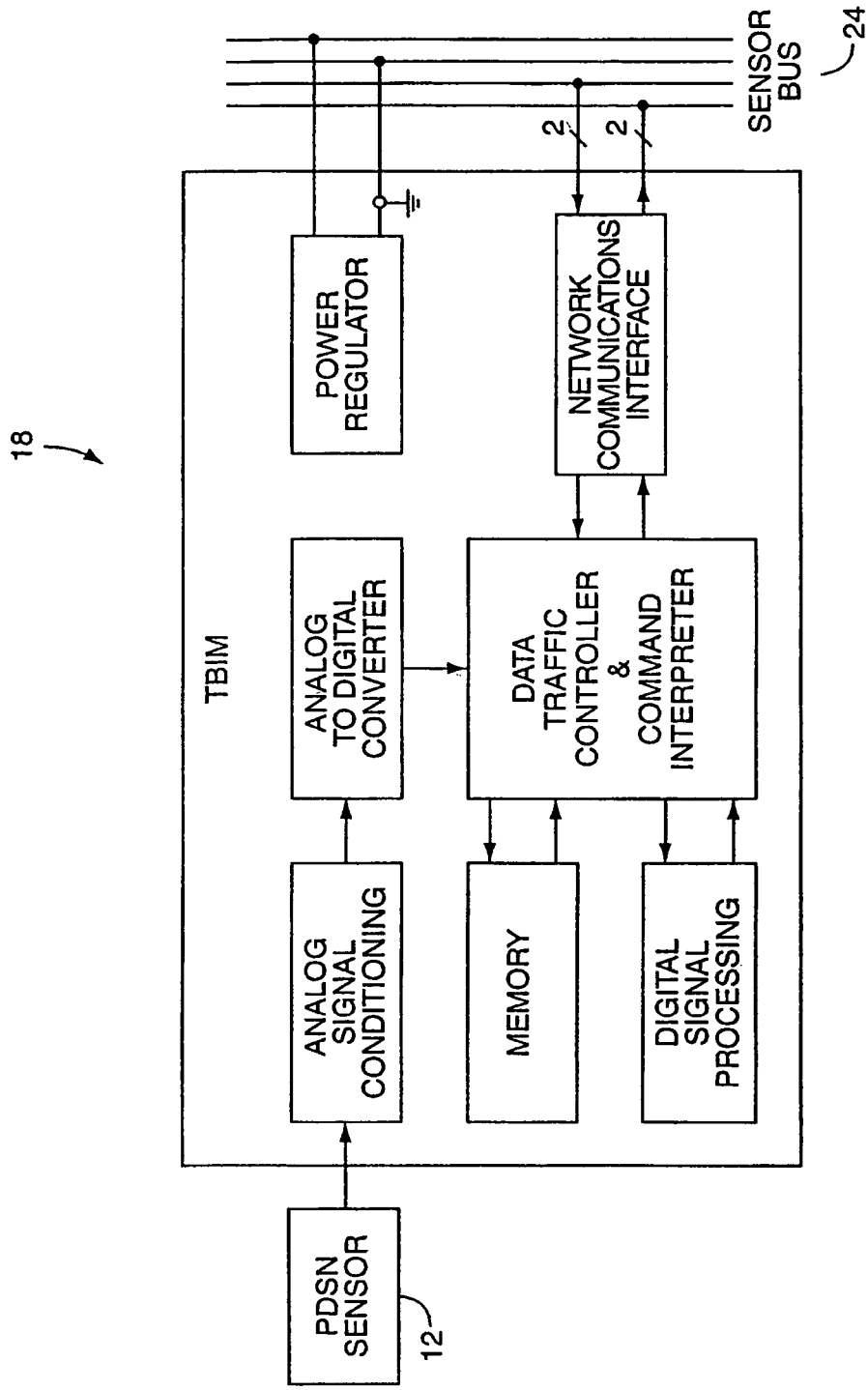
FIG. 4 is an enlarged block diagram of the signal processing module for the sensor array shown in FIG. 3.

As best seen in FIG. 4, an embedded electronic signal processing module 18 conditions the AE signal and performs the data processing. The signal processing module 18 itself is made of an analog ASIC (Application Specific Integrated Circuit), for analog signal conditioning, and a digital ASIC which performs the quantification, pattern recognition, timing, and short time data storage.

As best seen in FIG. 3, a digital data bus 24 provides communication between the signal processing modules 18 and the CPU 30. Further, this bus also powers the signal processing modules 18. The Transducer Bus Controller (TBC) is located in the CPU 30.

The CPU 30 assembles the processed information sent by the sensor nodes 14, and assesses any damage growth that may be occurring in the structure. A special feature of the earlier invention disclosed in commonly owned U.S. Pat. No. 6,399,939 is that the acoustic emission data processing takes place within the respective signal processing modules 18, and only the processed information is communicated outward through the interface bus 24. Furthermore, the fibers are connected in either series, parallel, or a combined series/parallel configuration to tailor the sensitivity of the sensor nodes 14 and match the environmental conditions under which it is operating. Bi-directional communication between the signal processing modules 18 and the CPU 30 takes place over the single digital data bus 24, thus eliminating cumbersome cables.

In operation, the CPU 30 initializes all sensor nodes 14, including their short-term clocks. The CPU 30 then queries each sensor node at time intervals of the order of a few tens of seconds to download the gathered information. The signal processing modules 18 and the sensor nodes 14 perform the digitization and analysis of the AE signals and store in a tabular form within its memory only those processed data that are recognized as related to damage growth for uploading to the CPU 30.

Among the parameters stored in the signal processing modules 18 are the time of occurrence of the AE event, energy content of the AE event, and the amplitude, duration, pattern, and other relevant parameters of the AE signal envelope. The TBC addresses each signal processing module 18 sequentially to upload the processed information from the signal processing modules 18, 18' permanently stored in CPU 30.

Figure 5:
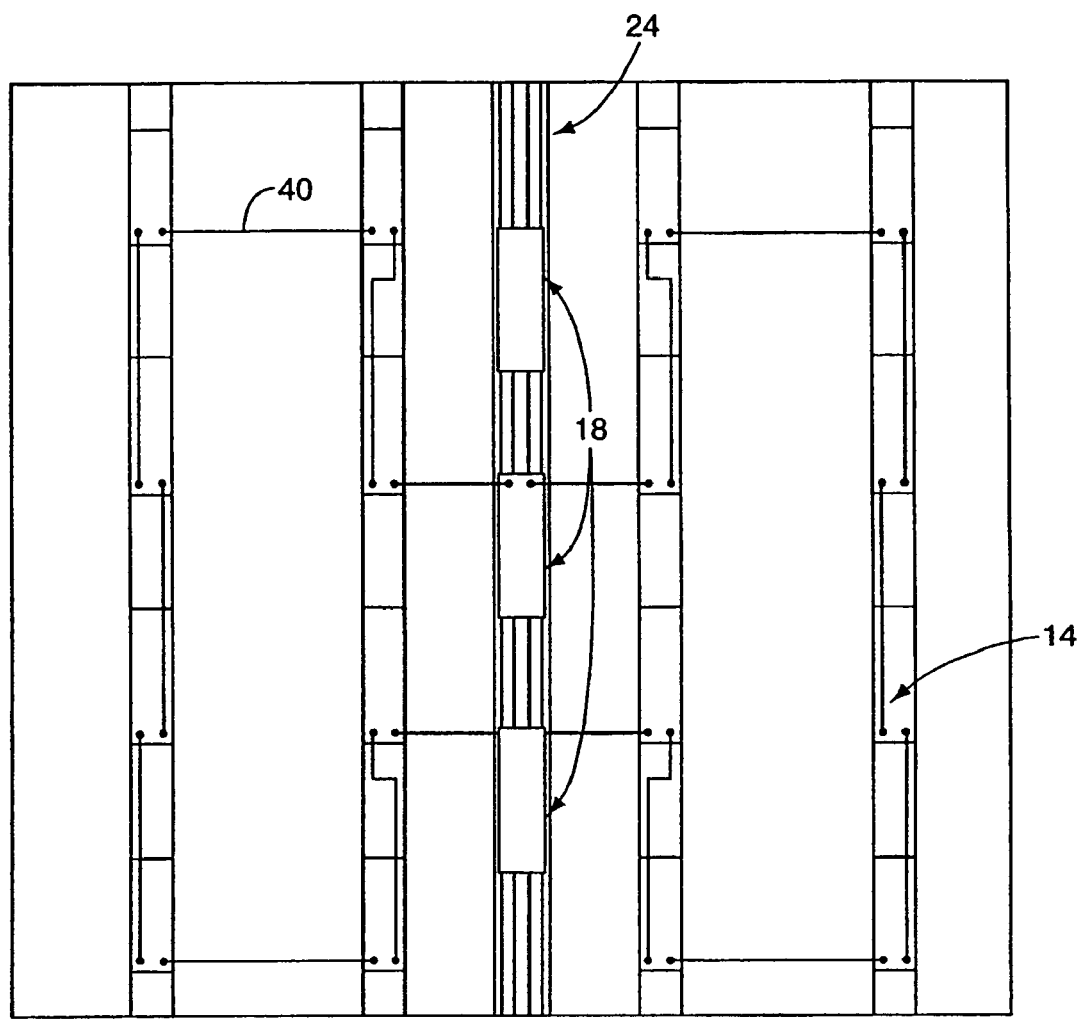
FIG. 5 is a top elevation view of the PZT fiber sensor array having a plurality of discrete sensor nodes connected in series and combined into a single output constructed according to the earlier invention disclosed in commonly owned U.S. Pat. No. 6,399,939.

As best seen in FIG. 5, the collection of sensor nodes 14 forms a unit cell 12 of a 'smart' composite material. The sensor array 10 can be constructed by embedding tens or hundreds of these sensor nodes 14 in laminated composite or textile composite structures. In the preferred embodiment, each of these sensor nodes 14 is formed from piezoceramic tapes whose segments act as independent sensor nodes 14 that detect damage to the structure by measuring AE waves generated by cracks in the material or breakage of fibers. The piezoceramic fibers can also potentially measure dynamic strains within the structure, which is useful for monitoring and regulating load paths within the structure to extend its safe life.

Active Fiber Composite (AFC) materials using PZT fibers (developed at MIT and commercialized by Continuum Control Corporation, Billerica Mass.) or ribbons (recently developed by CeraNova Corporation, Franklin Mass.) are preferably used to construct long continuous sensors. Interdigitated (IDT) electrodes are used to pole and electrically connect the sensor. The AFC is thermally stable, has a long fatigue life, provides great flexibility in tailoring and designing a sensor material, and is strong and rugged enough to be used on helicopters, in armor, and in layered composites. Because labor comprises most of the cost of producing the sensor tape, the use of a single ribbon effectively replaces six circular fibers, while still retaining the advantages of the fibers, and significantly reduces the cost of the distributed sensors.

Overall, the combination of fine piezoceramic fibers or ribbons with a flexible matrix provides a sensor material that is more robust and has a higher ultimate strain than the monolithic ceramics. The use of fibers or ribbons retains most of the stiffness of monolithic piezoceramic patches, and the unidirectional alignment creates the desired sensing/actuation in a single direction. The active fibers and structural fibers can be mixed within a single ply or can form separate plies in a composite. The overall laminate properties are found by a layer-wise integration of the constitutive equations for the layers. These properties are used in wave propagation simulations to determine the dynamic response of the sensor composite.

The electrode configuration can be designed to pole the fibers axially or through their thickness. Thin foil conductors (IDT electrodes) oriented perpendicular to the fibers are used on the top and bottom of the fibers. The conductors are used for both electroding and poling. The advantages of these designs are: (a) if the sensor is poled through the thickness of the fibers, the electrodes are easy to manufacture; (b) non-conductive structural fibers can be mixed with the sensor fibers, or conductive fibers can be put in adjoining layers; (c) the sensor can measure dynamic strains above 0.5 Hz.; (d) the sensor can be one cell of the system and AEs can be detected from all segments simultaneously; (e) the electrodes are deposited directly on the active fiber for ease of manufacturing and to allow a higher signal output when operating in the low field range; (f) ribbons which are larger than fibers and easier to fabricate can be used instead of fibers, making electroding easier and polarization more uniform; and (g) once encapsulated in a matrix, the ribbon can be woven as a straight fiber into textile composites. Both transverse and axial poling concepts are possible. In conventional AFCs, the electrodes are placed on the matrix above the fibers to prevent concentrations of the electric field in the fiber that can lead to locally high strains and fiber breakage. Because the fibers are used for sensing and not actuation, fatigue due to high electric field concentrations that normally necessitates use of the electroding above the fibers is absent. The electrodes are used for directly poling the sensor material.

Figure 6:
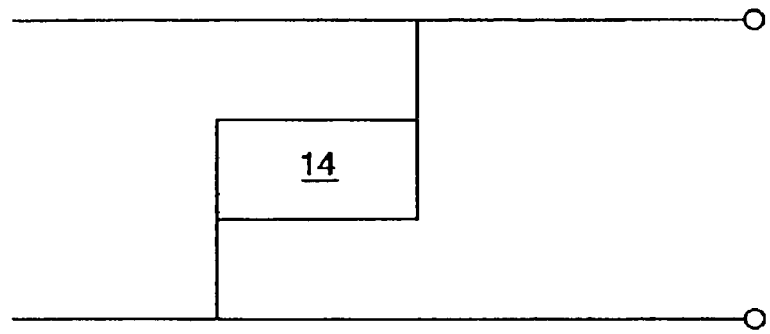
FIG. 6 is a simplified schematic of the bi-directional/single node PZT wafer sensor of the prior art, and the prior-art uni-directional/single node PZT fiber sensor shown in FIGS. 1 and 2.
Figure 7:
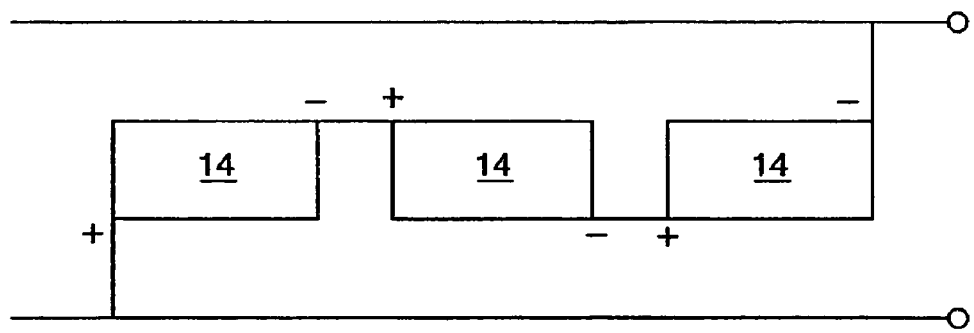
FIG. 7 is a simplified schematic of the sensor array shown in FIG. 5 that includes a plurality of discrete sensor nodes combined into a single output constructed according to the earlier invention disclosed in commonly owned U.S. Pat. No. 6,399,939.

As best seen in FIG. 6 (the prior art) and FIG. 7 (the earlier invention disclosed in commonly owned U.S. Pat. No. 6,399,939), the initial modeling that was performed to study the composite couples the elastic equations of a bar or plate structure to the piezoelectric constitutive equations and a parallel tuning electric circuit.

The piezoelectric equations to model a PZT or AFC sensor are:

$$\begin{bmatrix} D \\ T \end{bmatrix} = \begin{bmatrix} \varepsilon^S & e \\ -(e)^t & c^E \end{bmatrix} \begin{bmatrix} E \\ S \end{bmatrix} \quad (1)$$

where D is the electric displacement in coulombs/m$^2$, T is the stress in N/m$^2$, E is the electric field in volts/m, S is the strain, $\varepsilon^S$ is the clamped dielectric in Farads/m, e is the induced stress constant in Coluomb/m$^2$ or equivalently N/(m*volt), t is transpose, and $c^E$ is the constant field stiffness in N/m$^2$.

Considering a single axis, the equations in (1) are represented as:

$$D_j = \left( \varepsilon^S E(t) + e \frac{\partial w(x_j, t)}{\partial x} \right) \text{sgn}(j) \quad (2)$$

$$i_{gj} = \left[ C_j \dot{V}_o / K + e \frac{\partial^2 w(x_i, t)}{\partial x \partial t} \right] A_c \text{sgn}(j) \quad (3)$$

where j represents the jth segment of the sensor, w is the longitudinal displacement, V is the voltage, C is the capacitance of the piezoceramic, and the sgn function allows connection of the segments with positive or negative polarities. An electric circuit representing equations (2–3) for series connectivity is shown in FIG. 7.

An electrical parallel tuning circuit is connected to the acoustic emission sensor circuit to filter out the ambient vibration response to more accurately sense the acoustic emissions from cracks.

The combined equations for the electrical model of the AFC sensor and the connected tuning circuit are:

$$\begin{bmatrix} L_s & 0 \\ -L_p & L_p \end{bmatrix} \begin{bmatrix} \ddot{i}_l \\ \ddot{i}_s \end{bmatrix} + \begin{bmatrix} L_p/(R_p N C_p) & 0 \\ 0 & R_s \end{bmatrix} \begin{bmatrix} \dot{i}_l \\ \dot{i}_s \end{bmatrix} + \quad (4)$$

$$\begin{bmatrix} 1/(NC_p) & 1/(NC_p) \\ 0 & 1/C_s \end{bmatrix} \begin{bmatrix} i_l \\ i_s \end{bmatrix} = -\frac{A_e e}{NC_p} \begin{bmatrix} \sum_{j=1}^{ns} w_{xi}^j \text{sgn}(j) \\ 0 \end{bmatrix}$$

where is and il are the currents in the tuning circuit, R, L, $C_s$ are the circuit parameters, $C_p$, $A_e$, e are the sensor piezoceramic material parameters, and N, $w_{xi}^j$, sgn(j) are the number of sensor nodes, the strain rate at node j, and sign of the connectivity of node j.

An elastic model of a bar or plate is used to simulate the response of the sensor material subjected to AE or other excitation. The plate with the segments is shown in FIG. 9. The segments S1, S2, S3, S4, . . . S16 model the sixteen sensor segments of one fiber tape in the composite shown in FIG. 3. Since the AFC is poled using the electrodes, each segment acts as a uniform sensor. The segments can be spaced and connected in alternating polarity to cancel low frequency (<100 KHz) structural vibrations and the length of the segments can be matched to the half wavelength of the dominant stress waves to be measured.

This approach uses the continuous nature of the sensor as a spatial filter to cut-off the low frequency response that masks the AE response. If small segments are used, the continuous sensor can be designed similar to an acoustic wave filter to measure Lamb waves produced from damage propagation. Organic composites produce extensive AEs in the presence of damage. Thus, monitoring of AE in composites can be used as a passive method for damage detection. AEs in thin composite structures propagate as Lamb or plate waves. The two plate modes of AE waves observed in AE signals are the symmetrical, or extensional, wave and the anti-symmetric, or flexural, mode. Extensional plate waves contain higher frequency components and occur first in the signal, whereas the flexural waves contain lower frequency components, have higher amplitudes, and occur later in the wave. The extensional waves are non-dispersive (i.e., the wave velocity is independent of the wave number) and these plate waves can travel longer distances than dispersive waves. The flexural waves, on the other hand, are dispersive in nature and damage is more difficult to detect using these waves because the phase velocity and amplitudes change with temperature and small variations in boundary conditions.

Figure 8A:
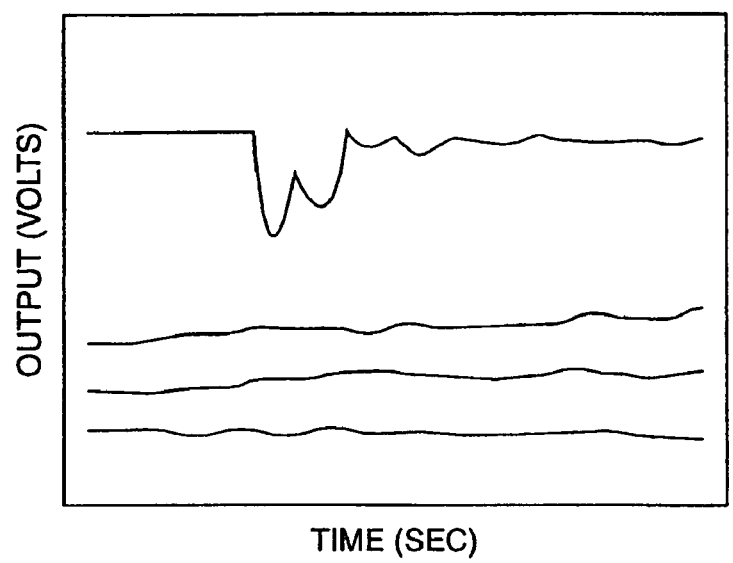
FIGS. 8A and 8B are graphs illustrating the effect of adding a plurality of discrete sensor node outputs into a single output.
Figure 8B:
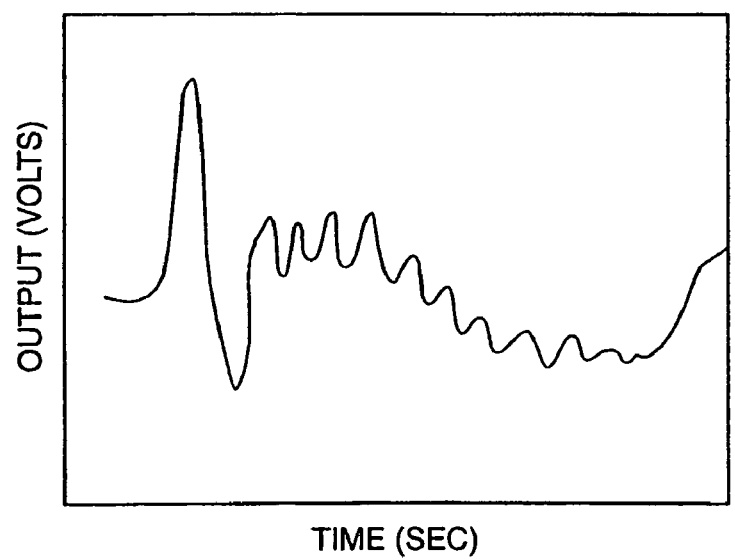

As best seen in FIGS. 8A and 8B, experiments have been performed to verify the characteristics and potential of the continuous sensor material. An AE event was simulated by breaking a pencil lead near sensor 1, and AE waveforms corresponding to four sensors were recorded using a digital oscilloscope, as shown in FIG. 8A. Sensor 1, which was nearest to the simulated AE source, registered the highest signal magnitude, and, more significantly, had higher frequency components present in the signal. Sensors 2, 3 and 4 had progressively fewer high frequency components in the signal, because high frequency components attenuate as a function of distance traveled more rapidly than low frequency components. Frequency components above 100 kHz were almost totally absent in these three sensors.

In practice, frequency components that are higher than 100 kHz can provide valuable information about the AE source. Obtaining those frequency components, however, would require a large number of AE sensors to monitor most structures. The weight, cost, and complexity of such a multi-channel instrument may be prohibitive.

Next, a distributed sensor was formed by connecting the four sensors to a single channel of a digital oscilloscope. A signal was generated by breaking a pencil lead near sensor 1. The signal detected from this arrangement is shown in FIG. 8B. The response of the continuous sensor was reduced in amplitude, but the high frequency components were preserved intact and the amplitude levels were still adequate for AE sensing. In this experiment, the optimal circuit design was not used. Had the optimal design been used, it would have increased the voltage output of the continuous sensor to be equal or greater than the output of a single sensor near the pencil lead break. In addition, smaller sensors would be used in practice.

Figure 9A:
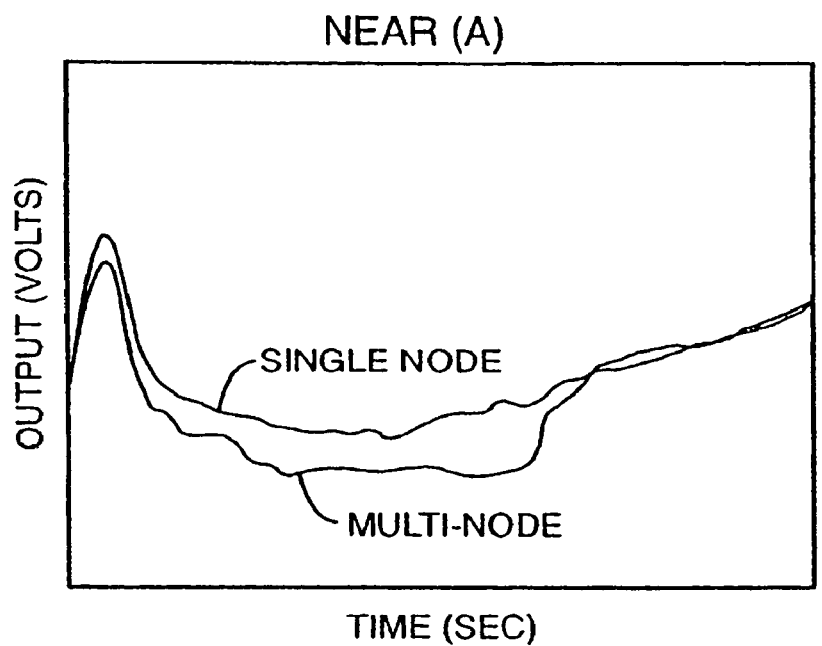
FIGS. 9A and 9B are graphs illustrating the difference between the response of a conventional single node sensor and the response of a multi-node sensor, and their dependence on the location of the structural event.
Figure 9B:
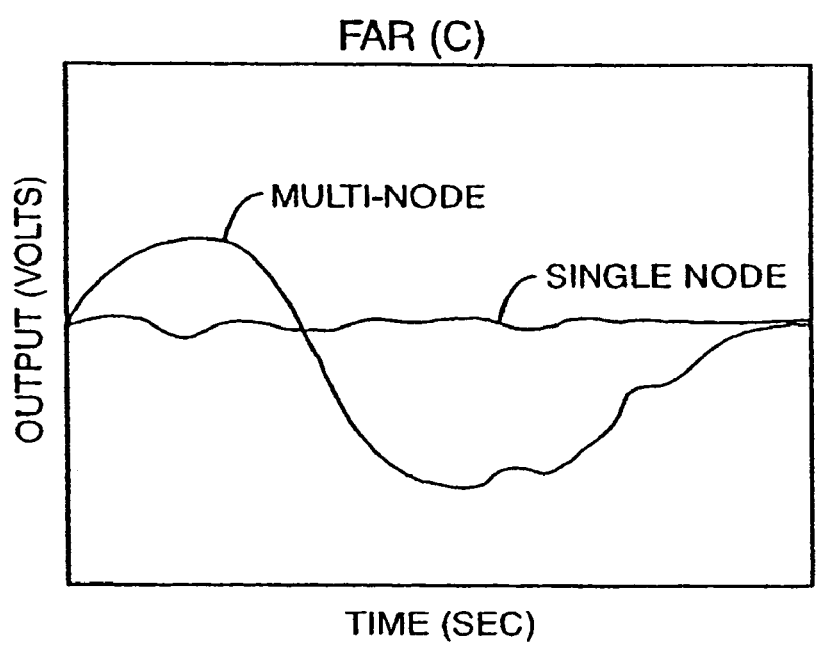
Figure 9C:
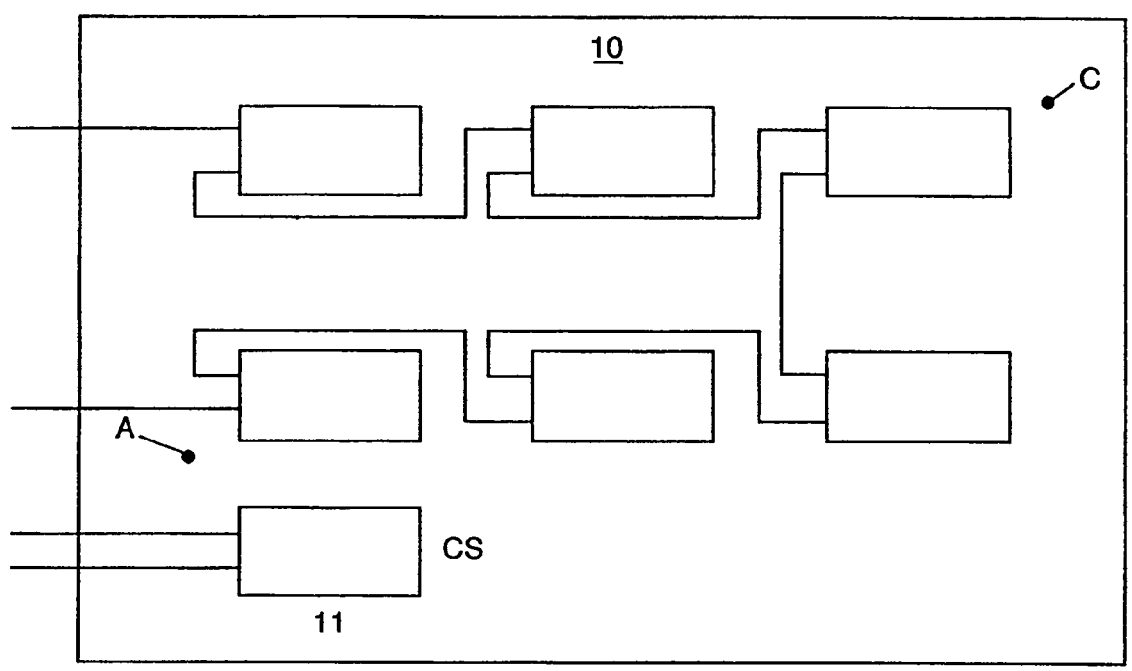
FIG. 9C is a schematic diagram showing the positions of a sensor array of the earlier invention disclosed in commonly owned U.S. Pat. No. 6,399,939 and a single sensor relative to acoustic emission events.
Figure 10:
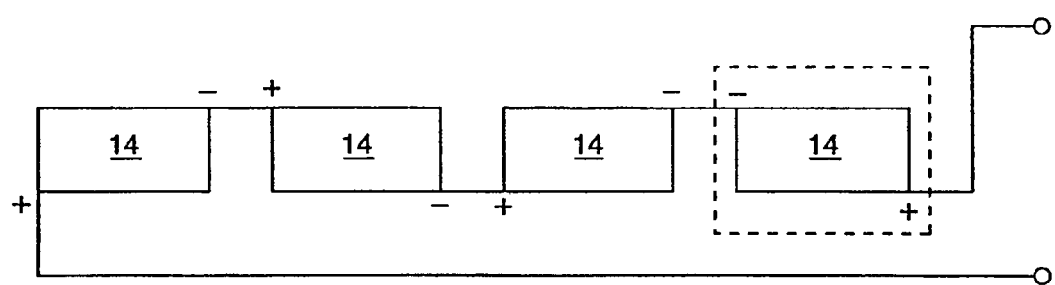
FIG. 10 is a simplified schematic of an alternative embodiment of the sensor array constructed according to the earlier invention disclosed in commonly owned U.S. Pat. No. 6,399,939 as shown in FIG. 5, including a plurality of discrete sensor nodes combined into a single output.

As best seen in FIGS. 9A and 9B, the output of a continuous sensor array 10 was compared to that of a single PZT sensor 11 for detecting an acoustic emission on a fiberglass panel, shown in FIG. 9C. A pencil lead break at location A in FIG. 9C is detected by both the continuous sensor array 10 and the conventional sensor 11. In contrast, the sensor response due to a pencil lead break at location C in FIG. 9C shows that the continuous sensor array 10 captures the signal while the conventional sensor 11 at CS cannot sense an AE signal that is originating at a point distant from the sensor.

In operation, the continuous highly distributed sensor system can monitor entire structures with a single digital data bus 24 and can thus eliminate the bulky coaxial cables and greatly reduce the hardware and communication needs for a field deployable health monitoring system. To illustrate this, consider an AE event occurring at a random location along a straight-line segment of length L, while this segment is monitored through N equally spaced AE sensors. The maximum distance that the AE signal travels to reach the closest sensor is d=L/(2N). The number of sensors required would be determined by the exponential rate of attenuation of AE voltage signals given by $V=A_o e^{-Kd}/N^a$ where $A_o$ is a signal amplitude coefficient, a is an exponent, and K is a material-dependent decay constant. The sensor array of the earlier invention disclosed in commonly owned U.S. Pat. No. 6,399,939 is able to minimize the exponents d and a in the above equation, thereby maximizing the possibility of detecting an acoustic event.

In order to train the sensor network, a procedure of calibrating each unit cell can be established. Although the different unit cells attached to a structure may be similar to each other, the dynamics and wave propagation characteristics may vary from point-to-point on the structure. Unless each signal processing module takes these differences into account when reducing the data, errors can be introduced in the quantification of the AE activity. The calibration procedure could establish the threshold levels, data acquisition time window, and other related parameters.

Finally, the software in the CPU 30 will be robust enough to identify the failure of a sensor or signal processing module 18. Redundancy can be built into the sensor network, such that most damages will be detected by more than one unit cell.

Among the advantages provided by the sensor array 10 of the earlier invention disclosed in commonly owned U.S. Pat. No. 6,399,939 are: (i) a drastic reduction of the weight, cost, and complexity of instrumentation; (ii) increased probability of detection of the acoustical event due to the reduction in the source-to-sensor distance; and (iii) a more faithful retention of the acoustical signature, including the high frequency components, of the source event in the signal transmitted from the distributed sensor, due to minimization of the source-to-sensor distance.

Since the high frequency components of an AE signal attenuate much faster than the low frequency components, the signal from the sensors will have little resemblance to the source event if the travel distance d is long. Conventional AE techniques quickly become impractical for most field-deployable health monitoring applications, as they require as many independent data acquisition channels as the number of sensors.

With the active composite continuous sensor of the earlier invention disclosed in commonly owned U.S. Pat. No. 6,399,939, an entire structure can be monitored by a group of continuous sensors or unit cells with N sensing elements, all connected to a single digital data acquisition bus. By increasing the number of sensor elements, it is possible to have access to the leading edge of the AE waveform before it is dispersed. Such access is crucial in identifying the source mechanisms and estimating the source magnitude. The AE source can be located within the region of a given distributed sensor and network algorithms will be developed to locate the damage more precisely for subsequent closer inspection and repair.

Certain modifications and improvements will occur to those skilled in the art upon a reading of the foregoing description. By way of example, the electrode pattern— specifically, the width and spacing of the AFC sensor segments—can be designed to optimize the voltage and current output of the sensor for a particular application. Transverse electroding and poling can be used instead of interdigital electrodes and can simplify the design and reduce the cost of the AFC sensor segments.

The continuous sensor segments of the earlier invention disclosed in commonly owned U.S. Pat. No. 6,399,939 can also be connected in four possible combinations to tailor the sensor characteristics, such as signal level and spatial filtering, for specific applications. The four combinations are: (i) an aligned series connection—i.e., (+−)(+−)(+−)(+−) . . . ; (ii) an alternating series connection—i.e., (+−)(−+)(+−) (−+) . . . ; (iii) an aligned parallel connection in which all positive terminals are connected to a common positive point and all negative terminals to a separate, common negative point; and (iv) an alternating parallel connection in which the parallel connection for the adjacent sensor nodes are reversed.

Besides acoustic emissions, the sensor array of the earlier invention disclosed in commonly owned U.S. Pat. No. 6,399,939 can measure different events—including peak strains, peak vibration levels, and stress wave propagation from impacts on the structure—that are pertinent to structural health monitoring. The large area coverage and simultaneous sensing can localize the event to a particular unit cell. The sensor array can be configured for integration into composite materials or attachment to the surface of metallic structures such as an aircraft. By having segments of the sensor array connected with different directional sensitivity, the unidirectionality of the active fiber composite sensor material can also be used to determine the location of events.

The individual sensor elements or nodes may also include an addressable switch that can be used to include or exclude that sensor element from the network of the sensor, thus providing a self-configuring sensor continuous sensor that can automatically adapt to operating conditions. The local processor can have the ability to address the switch and to configure the network of sensors to be employed at a given stage to monitor structure health. Communication between the local processor and the individual sensor nodes is established by either a local digital data bus or the signal leads.

Figure 11:
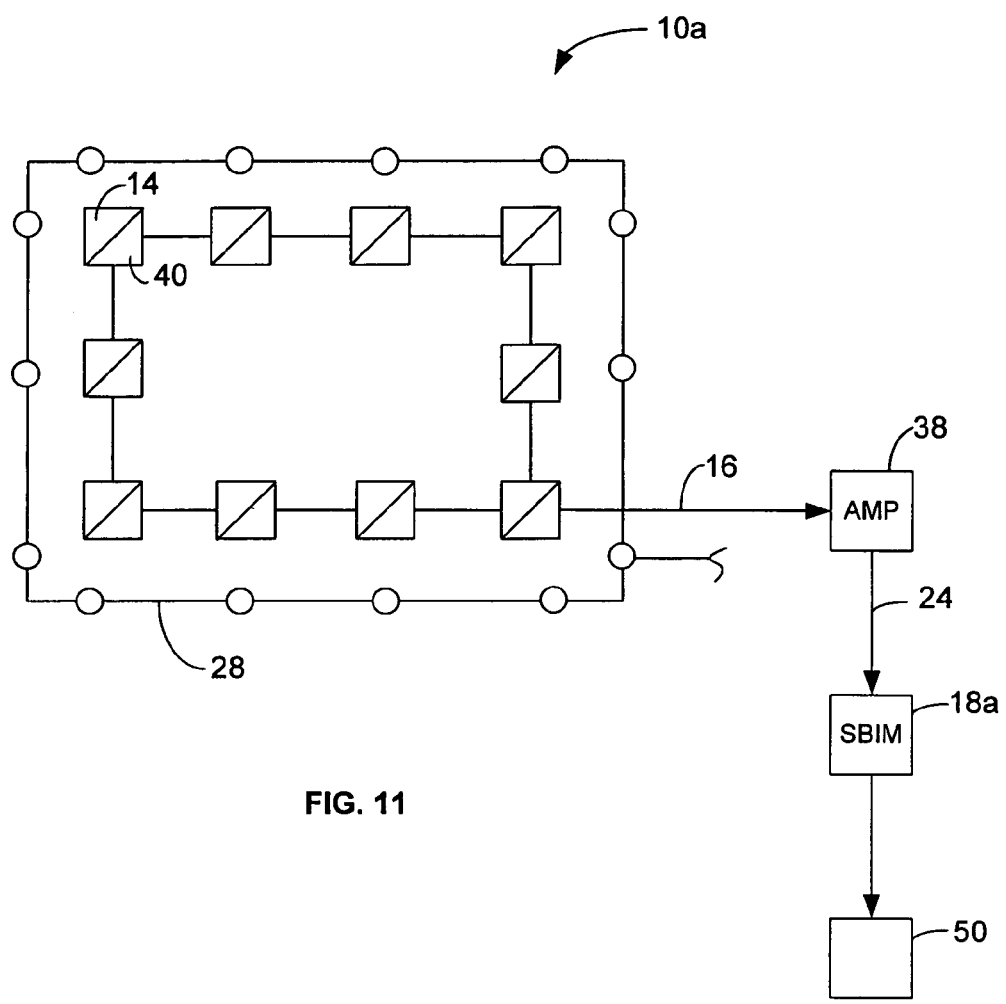
FIG. 11 is a block diagram of a sensor array including a plurality of discrete sensor nodes combined into a single output constructed according to the present invention.

As best seen in FIG. 11, a sensor array, generally designated 10, is shown constructed according to the earlier invention disclosed in commonly owned U.S. Pat. No. 6,399,939. The sensor array 10 includes three major subassemblies: a unit cell 12 having a plurality of discrete sensor nodes 14; a signal adder for combining the output of each of the discrete sensor nodes 14 into a single output 16; and at least one signal processing module 18a.

The plurality of discrete sensor nodes 14 may further be divided into discrete subgroups, each of the discrete subgroups located at a different structural location. The plurality of discrete sensor nodes 14 are electrically connected in series thereby forming a continuous series connection between each of the discrete sensor nodes.

A number of sensor node configurations are possible, for example, each of the discrete sensor nodes may include a chemical sensor or an accelerometer or a piezoceramic sensor. In the preferred embodiment, the piezoceramic sensor further comprises a plurality of piezoceramic fibers arranged in a planer array wherein the piezoceramic fibers are aligned substantially parallel to each other.

In the preferred embodiment, the signal adder 16 and the signal processing module 18a are connected in series. In addition, the apparatus may further including a signal amplifier 38, such as an impedance matched amplifier, connected between the signal adder 16 and the signal processing module 18a. Further, the apparatus may include a plurality of individual node signal amplifiers 40 connected between each of the discrete sensor nodes 14 and the signal processing module 18a. In the preferred embodiment, each of the node signal amplifiers 40 also is an impedance matched amplifier. Also, in the preferred embodiment, the sensor array may further include a guard array such as a guard ring 28 for improving signal quality.

Figure 12:
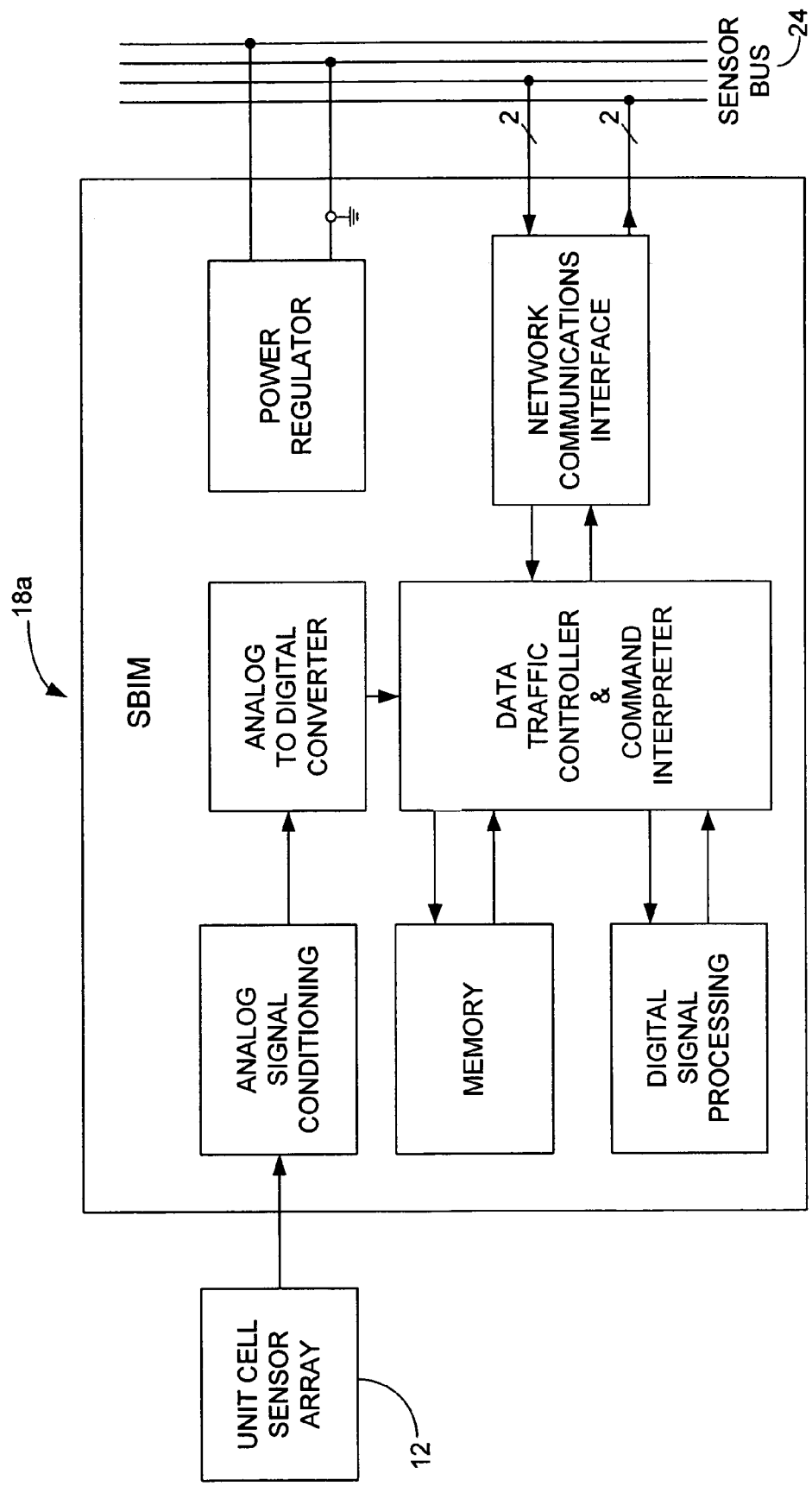
FIG. 12 is a enlarged block diagram of the signal processing module for the sensor array shown in FIG. 11 which is modified from the signal processing module shown in FIG. 3.

Unlike the earlier invention disclosed in commonly owned U.S. Pat. No. 6,399,939, signal processing module 18a uses the time interval between the electrical signals from each of the discrete sensor nodes 14 formed into a single sensor array output signal 24 to calculate the location of the critical structural event. As best seen in FIG. 12, the signal processing module 18a includes an input, a filter and an output on a timed scale to calculate the location of the critical structural event. The filter is at a predetermined band width. The predetermined bandwidth is calculated according to the Lamb wave propagation characteristics resulting from the acoustic emission pulse at the source location and by identifying one or more non-dispersive modes of this lamb wave to locate this acoustic emission source. Alternatively, it may be calculated using an electronic tag attached to each sensor that provides the ID number of the first hit sensor.

This process may be understood in greater detail by reference to the following article: Sundaresan, M. J., Schulz, M. J., Ghoshal, A., "Linear Location of Acoustic Emission Sources with a Single Channel Distributed Sensor," Journal of Intelligent Material Systems and Structures, Vol. 12, No. 10, pp. 689–700, October 2001. This paper and all of its references are hereby incorporated by reference in its entirety.

The signal processing module 18a conditions the AE signal and performs the data processing. The signal processing module 18a itself is made of an analog ASIC (Application Specific Integrated Circuit), for analog signal conditioning, and a digital ASIC which performs the quantification, pattern recognition, timing, and short time data storage.

A special feature of the earlier invention disclosed in commonly owned U.S. Pat. No. 6,399,939 is that the acoustic emission data processing takes place within the respective signal processing modules 18, and only the processed information is communicated outward through the interface bus 24. Furthermore, the fibers are connected in either series, parallel, or a combined series/parallel configuration to tailor the sensitivity of the sensor nodes 14 and match the environmental conditions under which it is operating.

However, in the earlier invention disclosed in commonly owned U.S. Pat. No. 6,399,939 locating damage on a bar needs a minimum of two independent signal processing instrumentation channels and locating damage on a plate needs a minimum of three such instrumentation channels. Thus, when multiple regions of complicated structures such as bridges, aircrafts, and space structures are to be monitored, the number of channels of instrumentation required for the conventional approach becomes numerous and hence unaffordable.

In the present invention, only one channel of AE instrumentation is required for locating the AE source within a region since the output on a timed scale is used to calculate the location of the critical structural event. Accordingly, instrumentation complexity, cost, and weight can be reduced by at least an order of magnitude, compared to conventional techniques.

Figure 13:
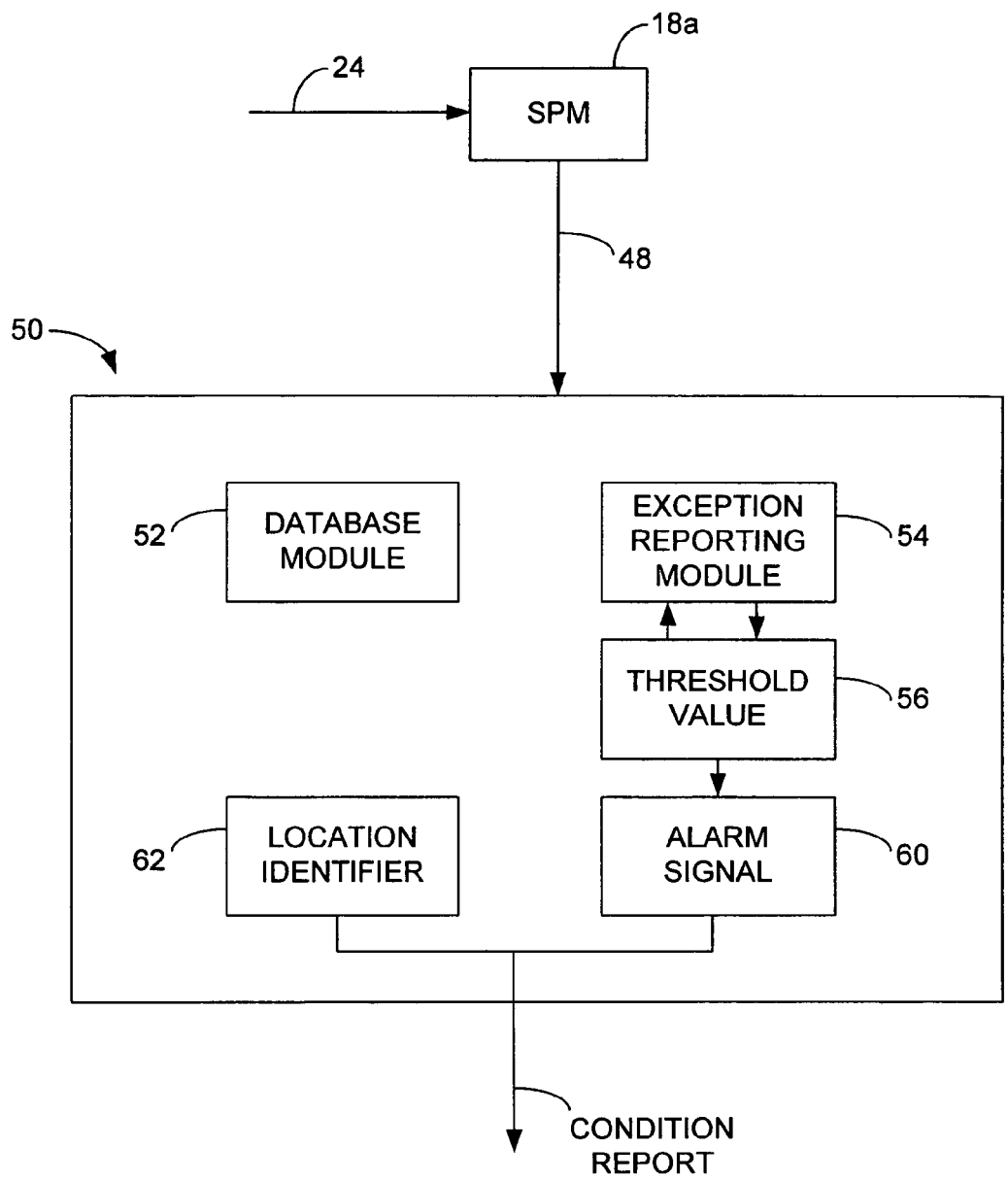
FIG. 13 is a block diagram of a data collection system downstream from the signal processing module.

As best seen in FIG. 13, a digital data bus 48 provides communication between the signal processing module 18a and the data collection system 50 downstream from the sensor processing module 18a. The data collection system 50 may include a plurality of various modules for recording and reporting events such as a database module 52 and an exception reporting module 54.

In the preferred embodiment, the exception reporting module 54 includes means for setting a predetermined threshold value and means for sending an alarm when the predetermined threshold value is met. Exception reporting module 54 may further include a station identifier for identifying the location of the alarm.

In operation, three or more piezoceramic (PZT) sensors, PVDF sensors, or other poled capacitive sensors are connected in series and attached to the structure. The output of these sensor nodes 14 are processed so as to extract specific modes of the Lamb waves that are propagating in the structure. After this processing, the signals corresponding to the signal arrival at each of the nodes of the continuous sensor are clearly separated. Further, by using the time interval between the signals from individual nodes, the location of the damage is calculated. The same procedure can be adopted for locating the damage in a plane by using a continuous sensor with a minimum of four sensor nodes. This procedure alone or in combination with neural network algorithm can be used for locating the damage and determining the severity of the damage event.

Thus, in the present invention the number of channels of acoustic emission instrumentation channels required for locating the AE source is reduced from three in the current techniques to one when the time scale algorithms are used for planar AE source location. Also, the number of channels of instrumentations for locating an AE source along a line, such as a pipe, is reduced from two channels to one channel. As a result, a significant reduction in the cost of onboard instrumentation becomes possible.

The present invention may be used in other areas where stress wave activity is monitored using multiple conventional sensors. This includes, but is not limited to: turbine engines where multiple conventional vibration sensors are used to detect resonant vibrations caused by flow and combustion instabilities; in rotating machinery to detect bearing damage or rotating unbalance; and for detecting damage in structures by monitoring stress wave propagation. In addition, the present invention may be used for monitoring the structural integrity of airplanes, space vehicles, bridges, nuclear reactors as well as other types of pressure vessels, oil rigs, etc.

Certain modifications and improvements will occur to those skilled in the art upon a reading of the foregoing description. It should be understood that all such modifications and improvements have been deleted herein for the sake of conciseness and readability but are properly within the scope of the following claims.

We claim:

1. A sensor array for non-destructively monitoring a structure to detect a critical structural event, said sensor array comprising:
   (a) a plurality of discrete sensor nodes, each of said discrete sensor nodes producing an electrical signal in response to a structural event;
   (b) a signal adder electrically connected to said plurality of discrete sensor nodes, said signal adder receiving and combining said electrical signal from each of said discrete sensor nodes to form a single sensor array output signal; and
   (c) a signal processing module for receiving and processing said single sensor output signal.

2. The sensor array according to claim 1, further including a data collection system downstream of said sensor processing module.

3. The sensor array according to claim 2, wherein the data collection system includes a database module.

4. The sensor array according to claim 3, further including an exception reporting module.

5. The sensor array according to claim 4, wherein said exception reporting module includes means for setting a predetermined threshold value and means for sending an alarm when the predetermined threshold value is met.

6. The sensor array according to claim 5, further including means for identifying the location of the alarm.

7. The sensor array according to claim 1, wherein said plurality of discrete sensor nodes are further divided into discrete subgroups, each of the discrete subgroups located at a different structural location.

8. The sensor array according to claim 1, wherein said plurality of discrete sensor nodes are electrically connected in series thereby forming a continuous series connection between each of said discrete sensor nodes.

9. The sensor array according to claim 1, wherein each of said discrete sensor nodes includes a chemical sensor.

10. The sensor array according to claim 1, wherein each of said discrete sensor nodes includes an accelerometer.

11. The sensor array according to claim 1, wherein each of said discrete sensor nodes includes a piezoceramic sensor.

12. The sensor array according to claim 11, wherein said piezoceramic sensor further comprises a plurality of piezoceramic fibers arranged in a planer array wherein said piezoceramic fibers are aligned substantially parallel to each other.

13. A sensor array for non-destructively monitoring a structure and to detect a critical structural event, said sensor array comprising:
(a) a signal adder electrically connected to a plurality of discrete sensor nodes, said signal adder receiving and combining said electrical signal from each of said discrete sensor nodes to form a single sensor array output signal; and
(b) a signal processing module for receiving and processing said single sensor output signal, whereby said signal processing module uses the time interval between said electrical signals from each of said discrete sensor nodes formed into a single sensor array output signal to calculate the location of said critical structural event.

14. The sensor array according to claim 13, wherein said signal adder and said signal processing module are connected in series.

15. The sensor array according to claim 14, further including a signal amplifier connected between said signal adder and said signal processing module.

16. The sensor array according to claim 15, wherein said signal amplifier is an impedance matched amplifier.

17. The sensor array according to claim 14, further including a plurality of individual node signal amplifiers connected between each of said discrete sensor nodes and said signal processing module.

18. The sensor array according to claim 17, wherein each of said node signal amplifiers is an impedance matched amplifier.

19. The sensor array according to claim 13, further including a guard array.

20. The sensor array according to claim 19, wherein said guard array is a guard ring.

21. The sensor array according to claim 13, wherein said signal processing module includes an input, a filter and an output on a timed scale to calculate the location of said critical structural event.

22. The sensor array according to claim 21, wherein said filter is at a predetermined band width.

23. The sensor array according to claim 22, wherein said predetermined band width is calculated according to the Lamb wave propagation characteristics resulting from the acoustic emission pulse at the source location and by identifying one or more non dispersive modes of this lamb wave to locate this acoustic emission source.

24. A sensor array for non-destructively monitoring a structure to detect a critical structural event, said sensor array comprising:
(a) a plurality of discrete sensor nodes, each of said discrete sensor nodes producing an electrical signal in response to a structural event;
(b) a signal adder electrically connected to said plurality of discrete sensor nodes, said signal adder receiving and combining said electrical signal from each of said discrete sensor nodes to form a single sensor array output signal;
(c) a signal processing module for receiving and processing said single sensor output signal, whereby said signal processing module uses the time interval between said electrical signals from each of said discrete sensor nodes formed into a single sensor array output signal to calculate the location of said critical structural event; and
(d) a data collection system downstream of said sensor processing module.

25. The sensor array according to claim 24, wherein the data collection system includes a database module.

26. The sensor array according to claim 25, further including an exception reporting module.

27. The sensor array according to claim 26, wherein said exception reporting module includes means for setting a predetermined threshold value and means for sending an alarm when the predetermined threshold value is met.

28. The sensor array according to claim 27, further including means for identifying the location of the alarm.

29. The sensor array according to claim 24, wherein said plurality of discrete sensor nodes are further divided into discrete subgroups, each of the discrete subgroups located at a different structural location.

30. The sensor array according to claim 24, wherein said plurality of discrete sensor nodes are electrically connected in series thereby forming a continuous series connection between each of said discrete sensor nodes.

31. The sensor array according to claim 24, wherein each of said discrete sensor nodes includes a chemical sensor.

32. The sensor array according to claim 24, wherein each of said discrete sensor nodes includes an accelerometer.

33. The sensor array according to claim 24, wherein each of said discrete sensor nodes includes a piezoceramic sensor.

34. The sensor array according to claim 33, wherein said piezoceramic sensor further comprises a plurality of piezoceramic fibers arranged in a planer array wherein said piezoceramic fibers are aligned substantially parallel to each other.

35. The sensor array according to claim 24, wherein said signal adder and said signal processing module are connected in series.

36. The sensor array according to claim 35, further including a signal amplifier connected between said signal adder and said signal processing module.

37. The sensor array according to claim 36, wherein said signal amplifier is an impedance matched amplifier.

38. The sensor array according to claim 35, further including a plurality of individual node signal amplifiers connected between each of said discrete sensor nodes and said signal processing module.

39. The sensor array according to claim 38, wherein each of said node signal amplifiers is an impedance matched amplifier.

40. The sensor array according to claim 24, further including a guard array.

41. The sensor array according to claim 40, wherein said guard array is a guard ring.

42. The sensor array according to claim 24, wherein said signal processing module includes an input, a filter and an output on a timed scale to calculate the location of said critical structural event.

43. The sensor array according to claim 42, wherein said filter is at a predetermined band width.

44. The sensor array according to claim 43, wherein said predetermined band width is calculated according to the Lamb wave propagation characteristics resulting from the acoustic emission pulse at the source location and by identifying one or more non dispersive modes of this lamb wave to locate this acoustic emission source.

45. The sensor array according to claim 43, wherein said predetermined bandwidth is calculated using an electronic tag attached to each sensor that provides the ID number of the first hit sensor.

* * * * *